United States Patent
Kearns et al.

(10) Patent No.: US 9,712,736 B2
(45) Date of Patent: Jul. 18, 2017

(54) ELECTROENCEPHALOGRAPHY (EEG) CAMERA CONTROL

(71) Applicant: Intel Corporation, Santa Clara, CA (US)

(72) Inventors: Phillip J. Kearns, Lake Oswego, OR (US); Andrew F. Lamkin, Beaverton, OR (US)

(73) Assignee: Intel Coprporation, Santa Clara, CA (US)

( * ) Notice: Subject to any disclaimer, the term of this patent is extended or adjusted under 35 U.S.C. 154(b) by 0 days.

(21) Appl. No.: 14/970,066

(22) Filed: Dec. 15, 2015

(65) Prior Publication Data

US 2017/0171441 A1   Jun. 15, 2017

(51) Int. Cl.
  *H04N 5/232*   (2006.01)
  *A61B 5/0476*   (2006.01)
  (Continued)

(52) U.S. Cl.
  CPC ......... *H04N 5/232* (2013.01); *A61B 5/04012* (2013.01); *A61B 5/0476* (2013.01);
  (Continued)

(58) Field of Classification Search
  None
  See application file for complete search history.

(56) References Cited

U.S. PATENT DOCUMENTS 6,575,902 B1 *  6/2003  Burton ............... A61B 5/18
                                                  340/575
9,319,980 B1 *  4/2016  Lewkow ............... H04W 52/02
(Continued)

FOREIGN PATENT DOCUMENTS

KR       101077661 B1    10/2011
WO    WO-2015047032 A1    4/2015

OTHER PUBLICATIONS

"Mindrider", [Online]. Retrieved from the Internet: <URL: http://dukodestudio.com/MindRider/, (2014), 1-7.
(Continued)

*Primary Examiner* — W B Perkey
(74) *Attorney, Agent, or Firm* — Schwegman Lundberg & Woessner, P.A.

(57) ABSTRACT

Various techniques for performing camera control techniques based on brainwave data from an electroencephalography (EEG) headset are disclosed herein. In an example, a computing system operates to receive brainwave data representing brainwave activity, process the brainwave data, and transmit a command to a camera device based on the processed brainwave data. For example, the brainwave data may correlate to raw brainwave signals (from gamma, beta, alpha, theta, or delta brainwaves), or composite brainwave signals (from multiple brainwaves, representative of attention, meditation, or like states). As a result, the computing system may transmit a command to a camera device to capture an image, a burst of images, start/stop video recording, or like commands for image and video operations, based on a human user's detected brainwave state. Further processing, detection, and training methods for brainwave control of camera operations are also disclosed.

30 Claims, 8 Drawing Sheets

(51) Int. Cl.
| | |
|---|---|
| H04N 5/44 | (2011.01) |
| H04N 5/76 | (2006.01) |
| G11B 27/34 | (2006.01) |
| A61B 5/00 | (2006.01) |
| A61B 5/04 | (2006.01) |
| H04W 4/00 | (2009.01) |

(52) U.S. Cl.
CPC ............ *A61B 5/6803* (2013.01); *G11B 27/34* (2013.01); *H04N 5/23293* (2013.01); *H04N 5/44* (2013.01); *H04N 5/76* (2013.01); *H04W 4/008* (2013.01)

(56) References Cited

U.S. PATENT DOCUMENTS

| | | | |
|---|---|---|---|
| 9,454,887 B1* | 9/2016 | Matalgah | G08B 21/06 |
| 2009/0281446 A2 | 11/2009 | Ludvig et al. | |
| 2010/0156617 A1* | 6/2010 | Nakada | A61B 3/113 340/439 |
| 2011/0279676 A1* | 11/2011 | Terada | A61B 5/0006 348/148 |
| 2013/0069985 A1* | 3/2013 | Wong | G02B 27/017 345/633 |
| 2014/0049627 A1 | 2/2014 | Gillette | |
| 2014/0221866 A1* | 8/2014 | Quy | H04W 4/206 600/544 |
| 2014/0347265 A1 | 11/2014 | Aimone et al. | |
| 2015/0033266 A1* | 1/2015 | Klappert | G06F 3/015 725/52 |
| 2015/0065907 A1* | 3/2015 | Lee | A61B 5/1101 600/544 |
| 2015/0338917 A1* | 11/2015 | Steiner | H04L 9/3231 345/156 |
| 2016/0296164 A1* | 10/2016 | Garcia Molina | A61B 5/0476 |
| 2016/0317056 A1* | 11/2016 | Moon | A61B 5/0482 |

OTHER PUBLICATIONS

"Neurowear "neurocam" concept movie", [Online]. Retrieved from the Internet: <URL: http://neurowear.com/projects_detail/neurocam.html, (2013), 1-4.

Cernea, Daniel, et al., "Detecting Insight and Emotion in Visualization Applications with a Commercial EEG Headset", SIGRAD, (2011), 53-60.

Gargiulo, Gaetano, et al., "A mobile EEG system with dry electrodes", (Dec. 2008), 1-4.

Healey, Jennifer, et al., "StartleCam: A Cybernetic Wearable Camera", (1998), 1-8.

Lutero, Leo, "Dog Camera Takes Photos According yo Your Pup's Heartbeat", Technology, [Online]. Retrieved from the Internet: <URL: http://www.psfk.com/2015/06/nikonasiadogcameraheartography.html, (Jun. 5, 2015), 1-6.

Terranova, Andrew, et al., "Seven Visions of Biohacking, Biosensing, and Biomimicry", [Online]. Retrieved from the Internet: <URL: http://makezine.com/2013/09/16/sevenvisionsofbiohackingbiosensingandbiomimicry/, (Sep. 16, 2013), 1-8.

"International Application Serial No. PCT/US2016/061968, International Search Report mailed Feb. 21, 2017", 3 pgs.

"International Application Serial No. PCT/US2016/061968, Written Opinion mailed Feb. 21, 2017", 9 pgs.

* cited by examiner

ELECTROENCEPHALOGRAPHY (EEG) CAMERA CONTROL

TECHNICAL FIELD

Embodiments described herein generally relate to the control and operation of electronic devices and, for some examples, the control and operation of electronic devices based on input from electroencephalography (EEG) brain activity monitoring devices.

BACKGROUND

The use of cameras and recording devices has greatly increased as electronic camera devices have adapted to a variety of form factors. For example, a variety of wearable cameras such as camera glasses (e.g., Google® Glass), helmet-cams, or other body-mounted (e.g., GoPro® cameras) form factors allow users to perform self-recording of activities from unique perspectives and points of view. However, wearable camera devices often encounter issues with limited memory spaces to capture video data, or involve manual user control to start or stop camera recording. Further, once video is captured, long periods of time (often hours) are involved to edit the video to the most interesting scenes.

BRIEF DESCRIPTION OF THE DRAWINGS

In the drawings, which are not necessarily drawn to scale, like numerals may describe similar components in different views. Like numerals having different letter suffixes may represent different instances of similar components. Some embodiments are illustrated by way of example, and not limitation, in the figures of the accompanying drawings in which.

DETAILED DESCRIPTION

Figure 1:
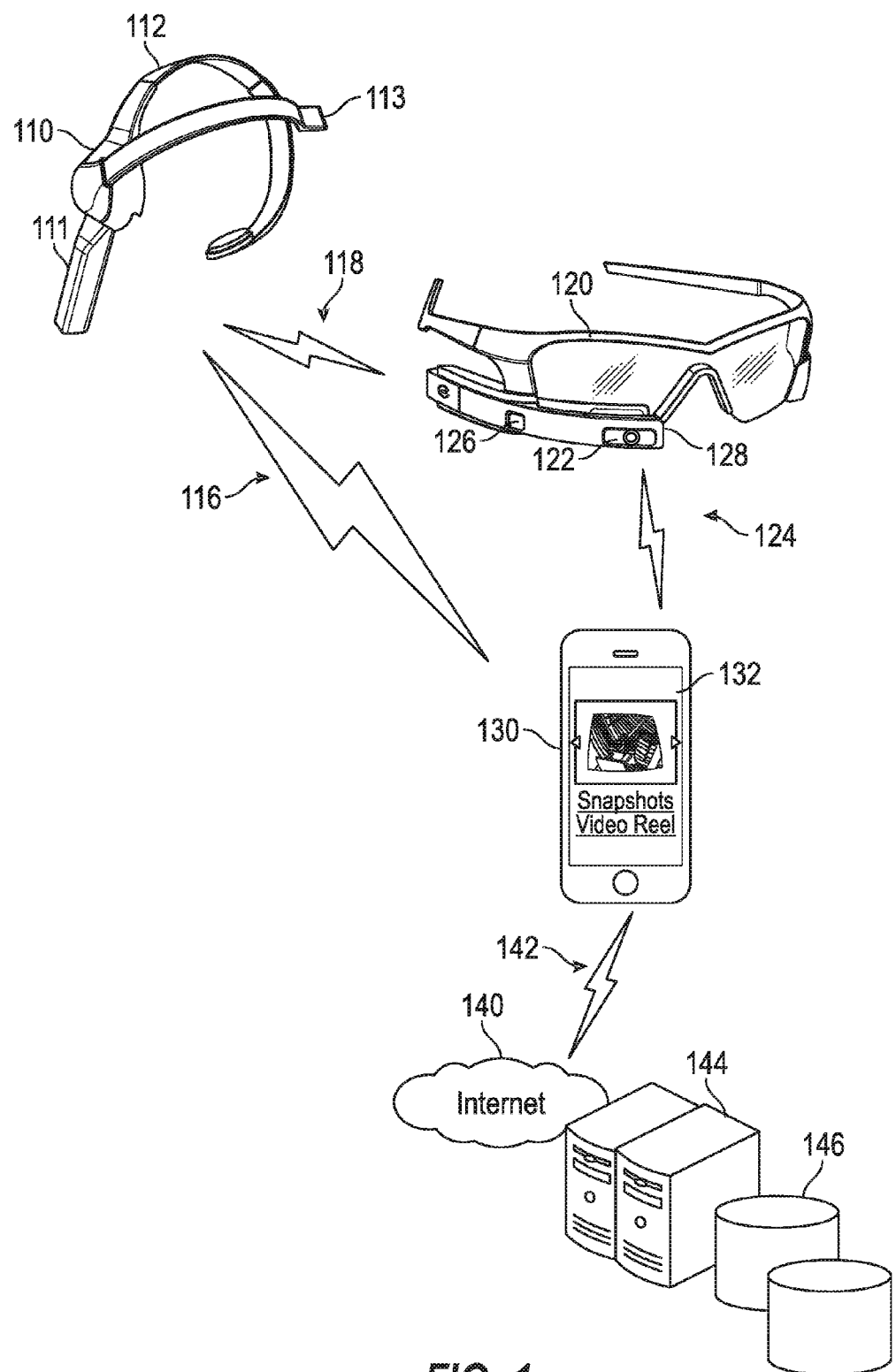
FIG. 1 illustrates a camera control use case overview involving an EEG headset, an electronic imaging device, and a mobile computing device, according to an example.

In the following description, methods, configurations, device components, and related apparatuses are disclosed that provide for camera control techniques based on EEG-based monitored values. Specifically, the following description includes various examples of a remote control for a camera allowing videos, photographs, and associated audio visual recordings to be triggered via readings from a neural oscillation (commonly referred to as "brainwave") sensor device.

In an example, the presently described techniques and configurations are applicable to the use of a computing device in wired or wireless communication with an EEG headset sensor unit and a camera. Based on the EEG data interpreted by the computing device, the camera and image capture operations for the camera may be controlled from raw brainwave data or via composite values derived from brainwave activity. For example, a human user may automatically trigger a camera video record or image capture activity based on the detection of certain brainwave signal levels of the human user exceeding a defined threshold, or based on attention and meditation composite brainwave levels exceeding a defined threshold.

As further discussed herein, a variety of camera activities and operations may be controlled as a result of brainwave activities. In an example applicable to the capture of multi-frame (video) content of a limited duration, this may include starting and stopping video and audio recording based on detected brainwave activity levels. In another example applicable to the capture of single frame (photo) content, this may include capturing a photo when certain brainwave activity is detected. Further camera activities that may be controlled may include establishing video markers, changing between a recording or photo capture mode, changing lens focus, changing exposure, zooming and panning, triggering a burst or timer mode, and like control methods applicable to single-frame and multi-frame audiovisual content capture from a recording device.

The form factors that have been developed for sport and body cameras are making a very large impact in how spectators view a variety of human activities, offering unique perspectives and insight. The desire to capture every exciting (or dangerous) moment with a camera competes with the problems of memory space, continuous fiddling to start or stop the camera, and potential hours spent editing the film to produce a relatively short clip of interest. The current state of the art for control of action cameras typically involves some form of manual input from the user via remote control or contact with the camera itself. This requires the user to disengage from what he or she is doing and physically interact with the camera controls to capture the desired recording. Thus, with existing camera controls, a user must either continually be starting and stopping video, or spend hours editing film afterwards, to capture the best moments of an activity.

Compared to the existing state of the art, the techniques described herein enable a human user to continue focus on what he or she is doing, while the EEG headset and the associated processing interprets the human user's brainwaves to control the camera and related image and video processing operations. This allows for the human user to obtain minutes of key points of film, as opposed to hours of recording, without having to manually control the camera. Accordingly, the techniques described herein may be applicable to a variety of scenarios such as action sports, life-blogging, movie filming, research and investigations, and in many other applications where a highlight reel is used. This highlight reel may be automatically generated (or generated with minimal user input) in a hands-free, non-invasive, and intuitive manner.

FIG. 1 illustrates a camera control use case overview, involving an EEG headset 110, an electronic imaging device 120, and a mobile computing device 130, according to an example. As shown, the EEG headset 110, the electronic imaging device 120, and the mobile computing device 130 are physically separate devices that are configured to wirelessly communicate with each other. In some examples, the features of the EEG headset 110 and the electronic imaging device 120 may be integrated into a single device (e.g., as an EEG headset/camera combination); in some examples, the features of the mobile computing device 130 may be integrated into the electronic imaging device 120 or the EEG headset 110 (e.g., as a camera or EEG device with built-in computing functionality); in some examples, the features of the electronic imaging device 120 may be integrated into the mobile computing device 130 (e.g., with use of a smartphone camera).

EEG headsets use sensitive electronics (e.g., a plurality of electrodes) to detect and analyze signals generated by neural activity in the brain. EEG headsets and accompanying electroencephalogram tests have historically been very large, expensive, and cumbersome, but the recent widespread availability of dry, compact EEG headsets on the market allows a compact and convenient method for reliably capturing data related to brain activity. The EEG headset 110 of FIG. 1 is shown in the form of a wearable, wireless dry sensor headset, including a first strap 112 that when worn extends over a top of a human user's head, a second strap 113 that when worn extends over the forehead of the human user's head, and a processing unit 111 that includes electronic processing circuitry for collecting and communicating information from the sensors of the first strap 112 and the second strap 113. The EEG headset 110, however, may take a variety of forms, such as in headset designs where a plurality of sensors are distributed across the head surface area (including in form factors where a plurality of sensor nodes project in different directions of a user's head when worn, such as in a configuration that resembles a "claw" or "spider-web"). It will be understood that the presently described techniques may be used with a variety of designs, shapes, and configurations of the EEG headset 110.

In one example, the EEG headset 110 collects data from a plurality of electrode sensors, positioned along a scalp of a human, to record voltage fluctuations resulting from ionic current flows among the neurons of the human brain. In addition to sensors integrated within or coupled to the EEG headset 110, the EEG headset may include various conductors, amplifiers, and digital circuitry to detect various types and levels of ionic current flows and translate such detected flows into electrical signals that represent the brainwaves. An example of the processing and sensor circuitry used in a "dry electrode" EEG recording device can be found in Gargiulo, Gaetano, et al. "A mobile EEG system with dry electrodes," Biomedical Circuits and Systems Conference, 2008, IEEE BioCAS 2008, which is incorporated by reference herein. However, it will be understood that the presently disclosed techniques may be used with a variety of other EEG sensors, recording device configurations, and headset form factors.

The electronic imaging device 120 of FIG. 1 is shown in the form of a wearable glasses set, which includes a camera 122 capable of image (still and video) recording. (In some examples, the camera 122 will also include or be coupled to a microphone for audio recording). The electronic imaging device 120 further includes sensors 126 and a projection display unit 128 for control of the electronic imaging device 120 using a heads-up display. It will be understood that the presently described techniques may be used with electronic imaging devices of varying capabilities and form factors, including electronic imaging devices that only include still image capture functionality.

The computing device 130 of FIG. 1 is shown in the form of a smartphone mobile computing device including a touchscreen display, with the touchscreen display presenting a graphical user interface 132. The computing device 130 may execute one or more software applications or operating system functions to receive data from, and transmit data to, the EEG headset 110 and the electronic imaging device 120. Additionally, the computing device 130 may use the graphical user interface 132 to provide controls for the image capture operations, provide a listing of captured image "snapshots" in a photo viewing interface (e.g., photo gallery), provide a listing of captured videos in a "snapshot" video playback interface (e.g., movie gallery), and provide other controls to establish the communication or operation of the EEG headset 110 or the electronic imaging device 120.

In an example, the audiovisual data obtained at the computing device 130 may be further communicated to another system or service for processing, storage, or archival. For example, the mobile computing device 130 may communicate audiovisual data captured from the camera 122 to a cloud-based media service 144, accessed via a network connection 142 via the internet 140. The cloud-based media service 144 may perform further storage, editing, or formatting of the data onto one or more data stores 146. In some examples, the data from the EEG headset 110 is also communicated to the cloud-based media service 144 for further processing and association with the audiovisual data.

In an example, data representing brainwave signals captured by the EEG headset 110 may be sent over a wireless communication link 116 to the computing device 130, at regular intervals or on-demand. On the computing device 130, a software program may operate to unpack and interpret the signals, to determine a brainwave state of the user. The software program may then interpret these actions to invoke certain camera control actions, and communicate such camera control actions in data commands sent to the electronic imaging device 120 via a communication link 124. These camera control actions may then trigger image capture and recording actions upon the camera 122 of the electronic imaging device 120. In some examples, communications and commands may occur via a communication link 118 established between the electronic imaging device 120 and the EEG headset 110 (e.g., to directly transmit sensor data from the sensors 126 or the camera 122 to the EEG headset 110, or to directly receive data of signals originating from the EEG headset 110 with built-in processing components of the electronic imaging device 120).

The signals communicated from the EEG headset 110 may include data indicating raw brainwave values (e.g., delta, theta, alpha, beta, and gamma waves), or composite values (e.g., combined raw brainwave values or scores) for brainwave activity representative of states such as attention and meditation. As further described herein, certain camera control actions may be associated with individual brainwave values, brainwave value thresholds, composite brainwave states, or other derived brainwave activity.

Figure 2:
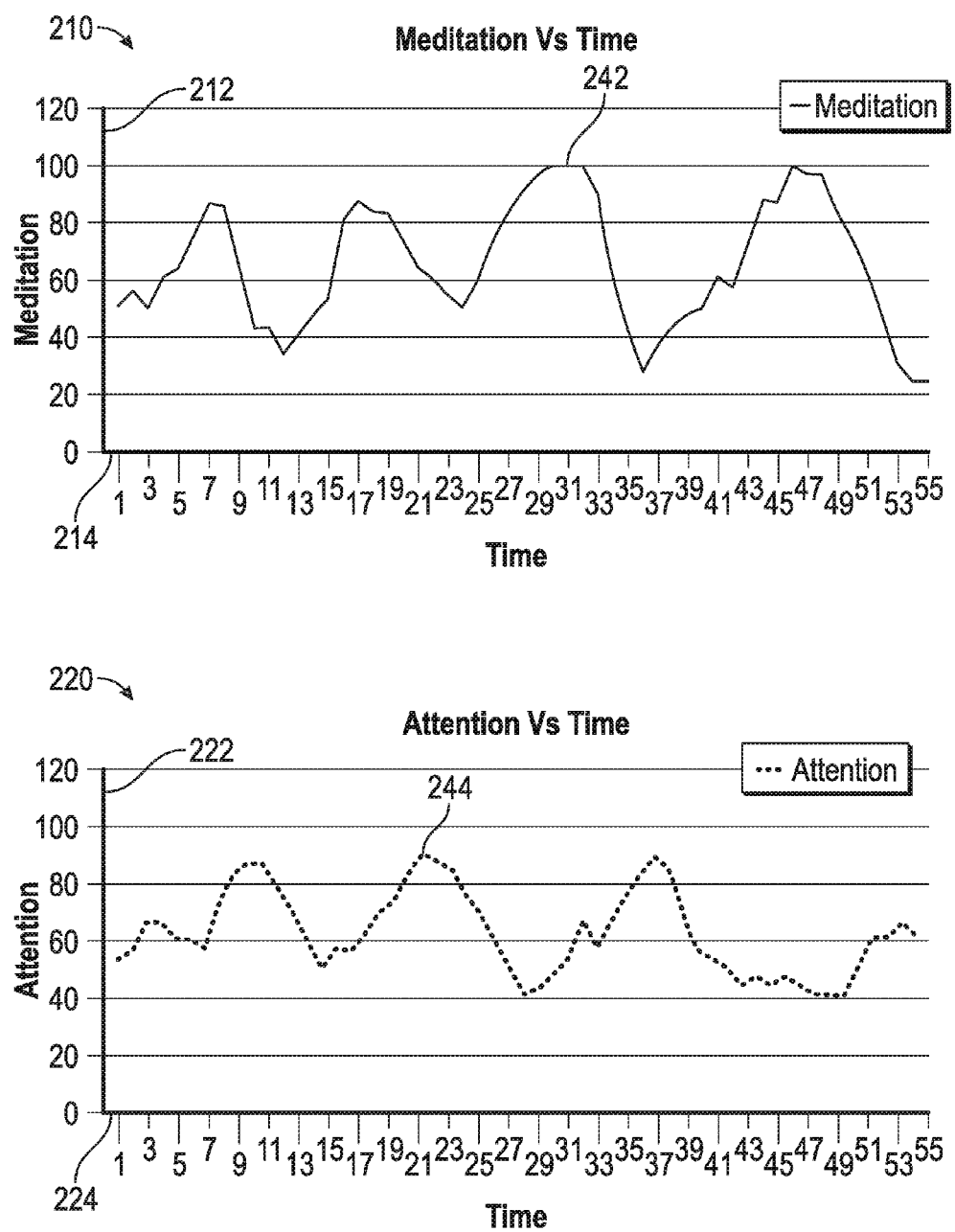
FIG. 2 illustrates an overview of captured inputs from an EEG headset for use with an EEG-based camera control technique, according to an example.

FIG. 2 provides an overview of captured inputs from an EEG headset for use with an EEG-based camera control technique, according to an example. Specifically, FIG. 2 depicts graphs 210, 220 of composite brainwave inputs captured from an example EEG headset, charted against an axis of time. The graphs 210, 220 depict composite values for meditation and attention, respectively, which may be based on some predetermined combination of raw brainwave values (e.g., delta, theta, alpha, beta, and gamma waves). These values may be measured relative to a defined measurement scale (using, in some examples, a defined measurement scale that is customized to a user or set of users).

As shown, the graph 210 depicts a meditation brainwave result 242 charted among an axis of meditation value measurements 212 (e.g., between values 0-120) over an axis of time 214 (e.g., between seconds 0 and 55). This graph 210 and related data representations of the meditation value measurements 212 may be processed in real-time, to trigger camera control actions in response to a value (e.g., a current detected value) of the meditation value measurements 212 exceeding a certain threshold.

Also shown, the graph 220 depicts an attention brainwave result 244 charted among an axis of attention value measurements 222 (e.g., between values 0-120) over an axis of time 224 (e.g., between seconds 0 and 55). The graph 220 and related data representations of the attention value measurements 222 may be processed in real-time, to trigger camera control actions in response to a value (e.g., a current detected value) of the meditation value measurements 212 exceeding a certain threshold.

In response to a monitored composite value exceeding a certain brainwave activity threshold, a series of commands (such as to trigger image snapshots) may be issued for control of a camera device over time. For example, based on data from graph 210, a camera may be triggered to capture an image every 1 second that the user is in a sufficient meditation state (e.g., over a meditation level of 80), which may be indicative of a user's focus on a particular item or activity occurring. Also for example, based on data from graph 220, a camera may be triggered to start video recording when a user's attention increases at a particular rate or stays above a certain threshold, and stop video recording when a user's attention decreases at a particular rate or goes below a certain threshold.

In an example, values from the EEG headset and derived outputs such as the graphs 210, 220 may be displayed to the user via a wired or wirelessly attached display interface (e.g., on a computing device graphical user interface). Various visualizations or current states may be displayed to the user in such a display interface, including: an indication of a detected brainwave activity/mental state; a camera image overlay relative to brainwave values; a camera state relative to brainwave values; and a comparison of camera settings to the log of composite brain activity. In some examples, the user may customize outputs and thresholds of composite (e.g., aggregated) or raw brainwave values using the graphical user interface. In some examples, the setting of thresholds and the accompanying graphical user interface interactions of brainwave values may occur during training operations, to adjust the sensitivity of the camera control to a particular user.

As a result, the presently disclosed techniques may be used to capture the moments of interest based on various derived emotions and mental activity from EEG measurements, such as where a human user is relaxed, angry, in a meditative state, and the like. This enables the control of a camera for capturing moments of interest in a real-life scenario, based on mental activity and derived conditions. A variety of pre-defined brainwave thresholds and levels may be used to determine such conditions.

Figure 3:
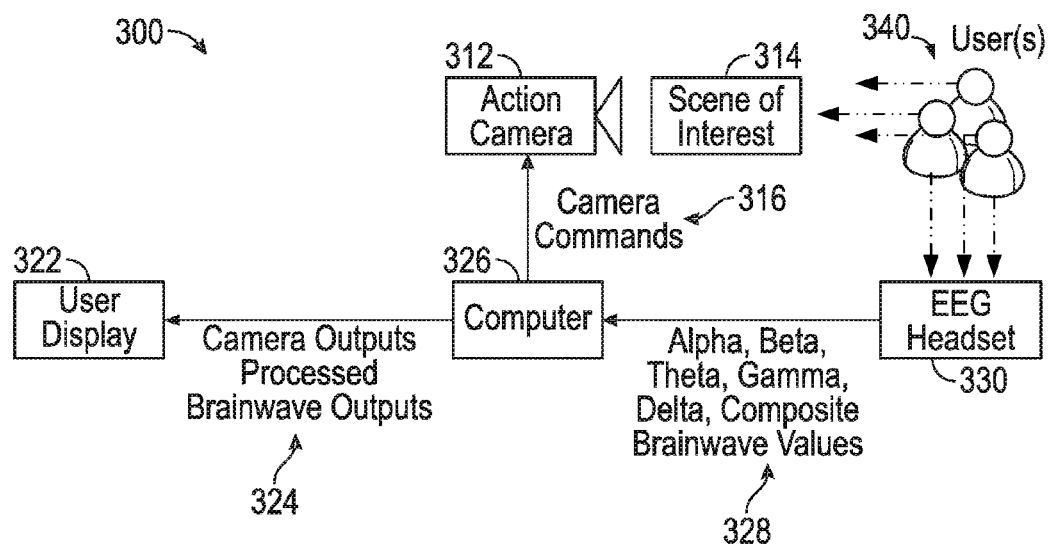
FIG. 3 illustrates a diagram of communications among an EEG headset, a camera, a computing device, and an output device, used with an EEG-based camera control technique, according to an example.

FIG. 3 illustrates a block diagram 300 of communications among an EEG headset, a camera, a computing device, and an output device, used with an EEG-based camera control technique, according to an example. In the block diagram 300, the flow of communication is depicted from an EEG headset 330 input device, to an action camera 312 input device (e.g., a standalone wearable camera), to and from a computing device 326 input/output device, and to a user display 322 output device.

As shown, the computing device 326 is communicatively connected to the EEG headset 330, and receives data representing alpha, beta, theta, gamma, delta, or composite brainwave data values 328, from one or more human users 340 observing the scene of interest 314. A software program on the computing device 326 receives and processes brainwave data values 328 from the EEG headset 330. As data is received, the software program unpacks it, analyzes, and records (and as applicable, stores and logs) the received brainwave data values 328. The software program checks the received brainwave data values 328 against camera control logic to determine whether the computing device 326 should transmit camera commands 316 to the action camera 312 to perform an action.

In an example, the camera commands 316 initiated by a camera control software program of the computing device 326 and communicated to the action camera 312 may include: start/stop video recording; perform a snapshot/photo burst/time lapse; start/stop audio recording. In some examples, the audiovisual data is captured exclusively at the action camera 312 (such as on an attached memory device); in other examples, the audiovisual data generated at the action camera 312 is communicated to the computing device 326 for capture in a storage medium of (or coupled to) the computing device 326. In some examples, the audiovisual data generated at the action camera 312 is communicated by the computing device 326 to a remote location such as an internet cloud storage and video processing service.

Thus, with ongoing operations, the camera control software program of the computing device 326 reads data from the EEG headset 330 and proceeds to transmit a series of the camera commands 316 to control the action camera 312 in response to the brainwave data values 328, user preferences, detected settings, and pre-programmed actions. In further examples, the brainwave data values 328 and other data from the EEG headset 330 may also be logged and displayed in the user display 322, and provided for feedback to the user in training and real-time display scenarios.

In some examples, the computing device 326 is in an ongoing, active state of electrical communication with the action camera 312 via a wired or wireless connection. The computing device 326 may be connected to the EEG headset 330 via a wired or wireless connection. A variety of local area or personal area wireless communication protocols (e.g., IEEE 802.11 Wi-Fi, BLUETOOTH®, etc.) may be used for such communications.

The action camera 312 may be provided by a body camera or like wearable device (e.g., glasses), an augmented reality device (e.g., goggles), or external device (e.g., smartphone, or connected camera device). In some examples, the computing device 326 may be integrated into a common wearable device as the action camera 312, including processing circuitry to operate the software program and a graphical user display through an augmented reality display.

The video or graphical content created with use of the present camera control techniques may be obtained and persisted in a number of forms. In an example, analysis of data obtained from the EEG headset 330 may be used to automatically generate the camera commands 316 to the action camera 312 to start and stop recording based on certain brainwave activities. For example, for an action camera 312 that would otherwise be configured to capture video of an entire event, the brainwave activity may be used to obtain a "highlights reel" of clips of interesting activities and content, triggered from brainwave activity that varies over time. In some examples, the action camera 312 is configured to continue recording continuously, but the generation of the highlights reel may be created through a metadata listing of relevant times, frames, or other metadata corresponding to brainwave activity.

In some examples, the presently described EEG camera control techniques may be used to capture content from a camera that is not attached but located proximate to the wearer of the EEG headset. (For example, one trained user may operate the brainwave control interface, and another user may hold or operate the camera). In another example, brainwave activity may be used to have a user, a friend nearby, or an observer generate the signals of interest (such as intense focus and concentration) to trigger a remotely-located camera. In some examples, the control techniques may also be integrated with brainwave signals obtained from EEG headsets from multiple users (e.g., to begin video recording when a sufficient number of users have reached certain brainwave activity levels). In some examples, the brainwave activity may be correlated or referenced to other biosignal measurements from human or external sources. Such signals may be obtained through electrical, fluidic, chemical, or magnetic sensors.

Figure 4:
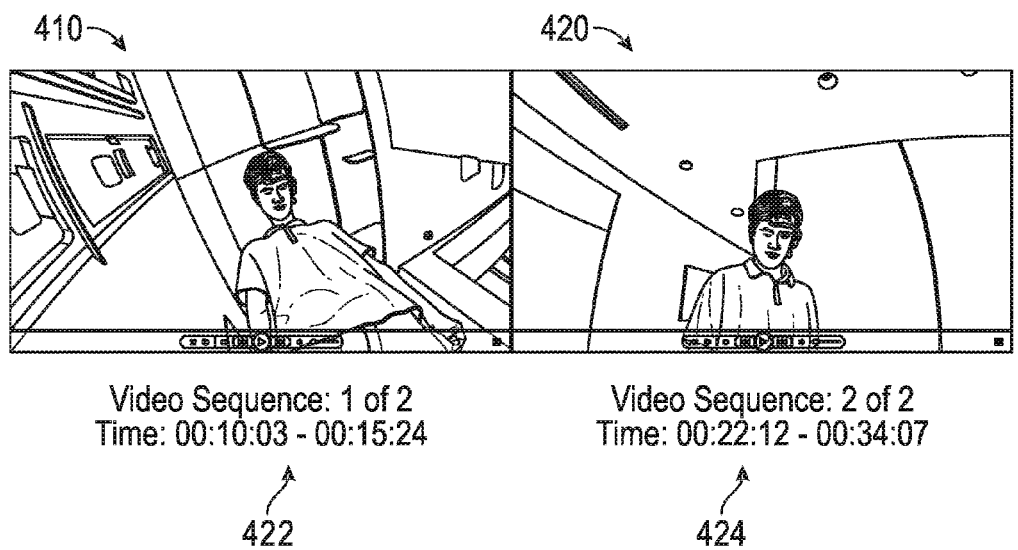
FIG. 4 illustrates an overview of video output produced with an EEG-based camera control technique, according to an example.

FIG. 4 illustrates an overview of video output produced with an EEG-based camera control technique, according to an example. As shown, a series of video outputs, a first video sequence 410 and a second video sequence 420, depict a brainwave-triggered capture of a video of an EEG-headset user using an external action video camera. Further, the first video sequence 410 and the second video sequence 420 are associated with respective video metadata characteristics, represented by a first video metadata set 422 and a second video metadata set 424.

Video recording of the first video sequence 410 and the second video sequence 420 may be triggered in response to multiple types of brainwaves, such as in response to the individual brainwave thresholds or composite brainwave activity thresholds as previously described. Through training or other user interaction, the user may set a threshold value of certain brainwave values so that the video may record the moments when the user's brainwave activity is above (e.g., is exceeding or stays above) this threshold.

In some examples, crossing a brainwave activity threshold may be used as a trigger for setting a marker of a beginning or ending of an ongoing video recording stream, or to control video recording (or data storage or transmission) activity. For example, decreasing below a meditation value threshold may start recording activity for a video, and the video continues recording while the user leaves the meditative state, stopping only when the user again reaches a meditative threshold. In other examples, an instantaneous mental state may be used as a control.

The metadata values that are obtained during capture of a video sequence may include timing values, including start, stop, or points of interest during recording. For example, the first video metadata set 422 and second video metadata set 424 may be associated with respective video sequences of a larger video segment, being identified based on certain brainwave activity levels. Other metadata values may be recorded or activated based on such brainwave activity levels.

Figure 5:
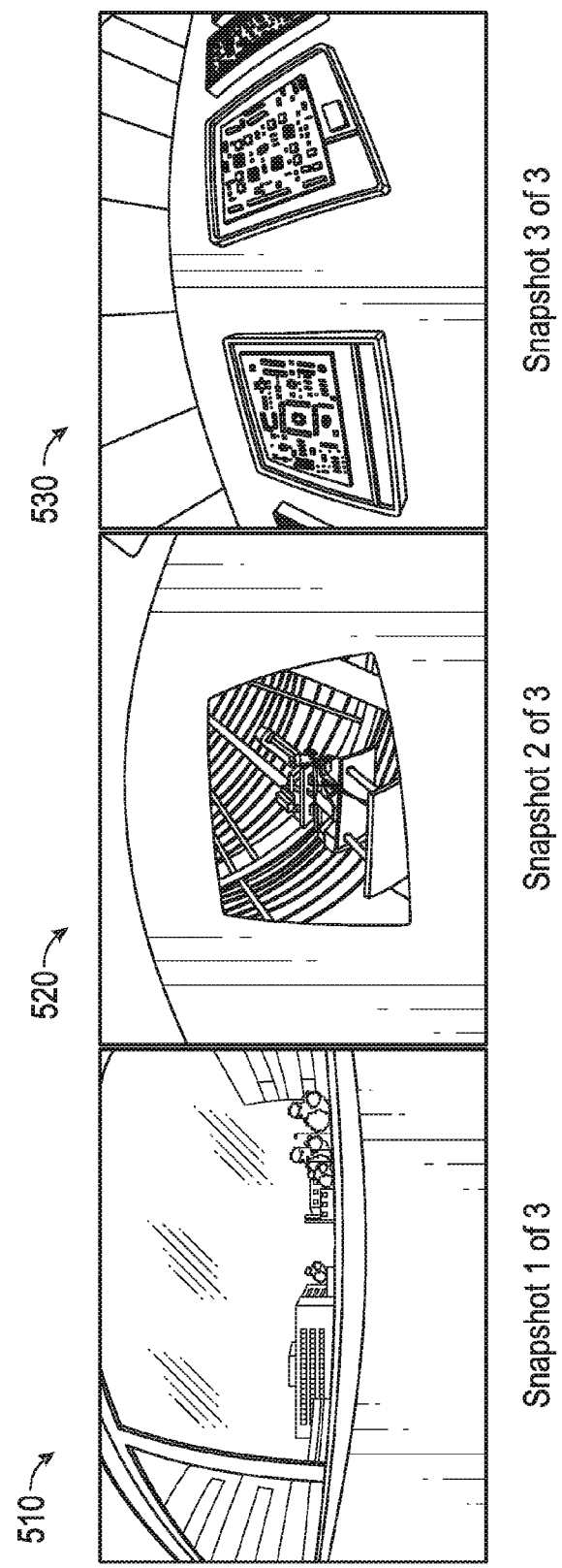
FIG. 5 illustrates an overview of an image capture output, in the form of snapshots, produced with an EEG-based camera control technique, according to an example.

FIG. 5 illustrates an overview of an image capture output, in the form of snapshots 510, 520, 530, produced with an EEG-based camera control technique. As shown, each of the snapshots 510, 520, 530 relate to pictures captured over a period of time from a human-oriented camera, with the capture activity being triggered based on a user's attention level (determined from a composite brainwave measurement).

For example, snapshot 510 may occur in response to an attention composite brainwave trigger (e.g., from a user observing bright sunlight or other stimuli of an outdoor setting); snapshot 520 may occur in response to an meditation composite brainwave trigger (e.g., from a user observing artwork for a period of time); and snapshot 530 may occur in response to a beta rhythm brainwave trigger (e.g., from a user observing or reading text about multiple objects of interest for a period of time).

The presently described techniques for brainwave camera control provide applicability beyond simple wearable action camera use cases. For example, the presently described techniques may be used as an ethnographic tool for monitoring, documenting, and analyzing images of what sparks a true attention grab in certain people, or what visual stimuli contributes to relaxation or meditation states. Additionally, various multi-user settings may be implemented to enable such monitoring.

The present EEG camera control techniques, as well as software programs for documenting and graphing EEG activity over time, has potential uses in a variety of industries and disciplines. For example, in a healthcare setting, the continual monitoring provided by a mobile EEG-controlled camera could serve to document the occurrence of an epileptic seizure or a stroke and the visual stimulus that caused it. This would allow for clinicians to more accurately analyze the types of visual stimuli that trigger a negative response. Likewise, in other healthcare settings, such EEG camera control techniques could be used to detect visual stimuli from video in patients during a healthcare procedure or examination, or to provide feedback from patients who have limited mobility or ability to react. As another example, a doctor may operate an EEG-controlled camera to capture photographs of various aspects of a patient as a medical procedure is being performed, including events in which stressors, difficulty, challenge, excitement, or high attention is being experienced.

Further, the presently disclosed EEG camera control techniques may be used in recreational environments (e.g., sports), workplace environments, and specialized applications (e.g., healthcare providers, engineering, maintenance work). Inspection, auditing, and observation use cases may also benefit from the presently described techniques. In a maintenance setting, an inspector may operate an EEG-controlled camera to capture evidence of inspection areas, and review the snapshots or video of areas of interest at a later time. An inspector scanning a plane, for example, may devote a lot of attention to a particular part of interest (e.g., a rusty bolt), and the video or snapshot taken could provide data for later review of detected issues, or verification of the quality of the inspection. The video recordings could be combined with contextual data including location and orientation to provide an automated record of the inspection. Accordingly, the presently disclosed techniques may be used to capture areas of interest that were noticed, unusual, broke concentration, or otherwise notable items.

Figure 6:
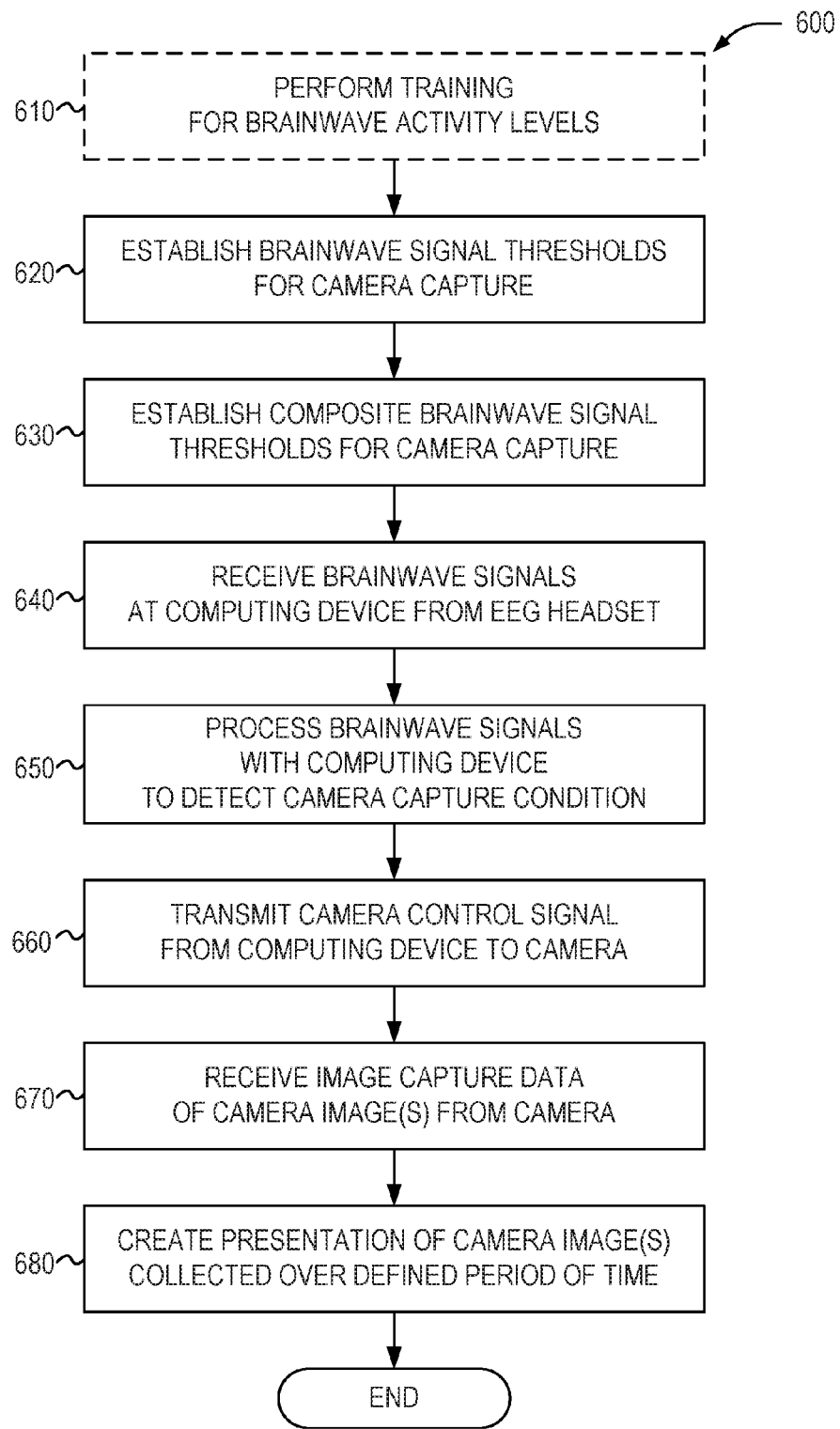
FIG. 6 illustrates a flowchart of a method for capture of image data with an EEG-based camera control technique, according to an example.

FIG. 6 illustrates a flowchart 600 of a method for capture of image data with an EEG-based camera control technique, according to an example. In an example, the method of flowchart 600 is executed by a computing device such as a mobile computing device (e.g., smartphone or tablet) that is connected to an externally located EEG headset and camera components. As shown, the flowchart 600 is indicated for the capture of a static image (or bursts of static images), but it will be understood the following techniques may be modified for use with video or composite photo-audiovisual recordings.

As shown, the flowchart 600 includes a performance of training for brainwave activity levels (operation 610), which in some examples, is optional. Such training may involve uses of mobile device graphical outputs, flashing LED feedback, external simulative feedback (e.g., vibration, light, sound, etc.), or the like, to provide feedback on a user's current brain activity state and when certain brainwave events occur. In other examples, default values may be used in lieu of training, or training may be integrated into an ongoing process rather than being performed prior to the image capture activity.

The flowchart 600 includes operations for establishing brainwave signal thresholds for a camera image capture (operation 620) and establishing composite brainwave signal thresholds for a camera image capture (operation 630). These thresholds may be obtained from the aforementioned training, provided as default values, or be partially or wholly user-controlled.

During operation of the EEG headset device, the mobile computing device may receive data for detected brainwave signals (operation 640) and proceed with processing operations for the detected brainwave signals (operation 650) to detect a camera capture condition. As discussed herein, a detected camera capture condition may be based on raw or composite brainwave levels that exceed a threshold at a point in time, over a period of time, or using other measurements.

In response to a camera capture condition, the computing device may transmit a camera control signal to the camera device (operation 660). Thereafter, the camera device will record the one or more image frames and transmit image data of the one or more image frames to the computing device, which is received by the computing device (operation 670). Based on the received data, the computing device may further store, process, or transmit the image data, such as creating a presentation (e.g., camera roll) of camera images collected over a defined period of time (operation 680). Further user interaction may occur before, during, and after the capture of the image data, to further specify which types of images (and which brainwave activity) is captured or presented.

Figure 7:
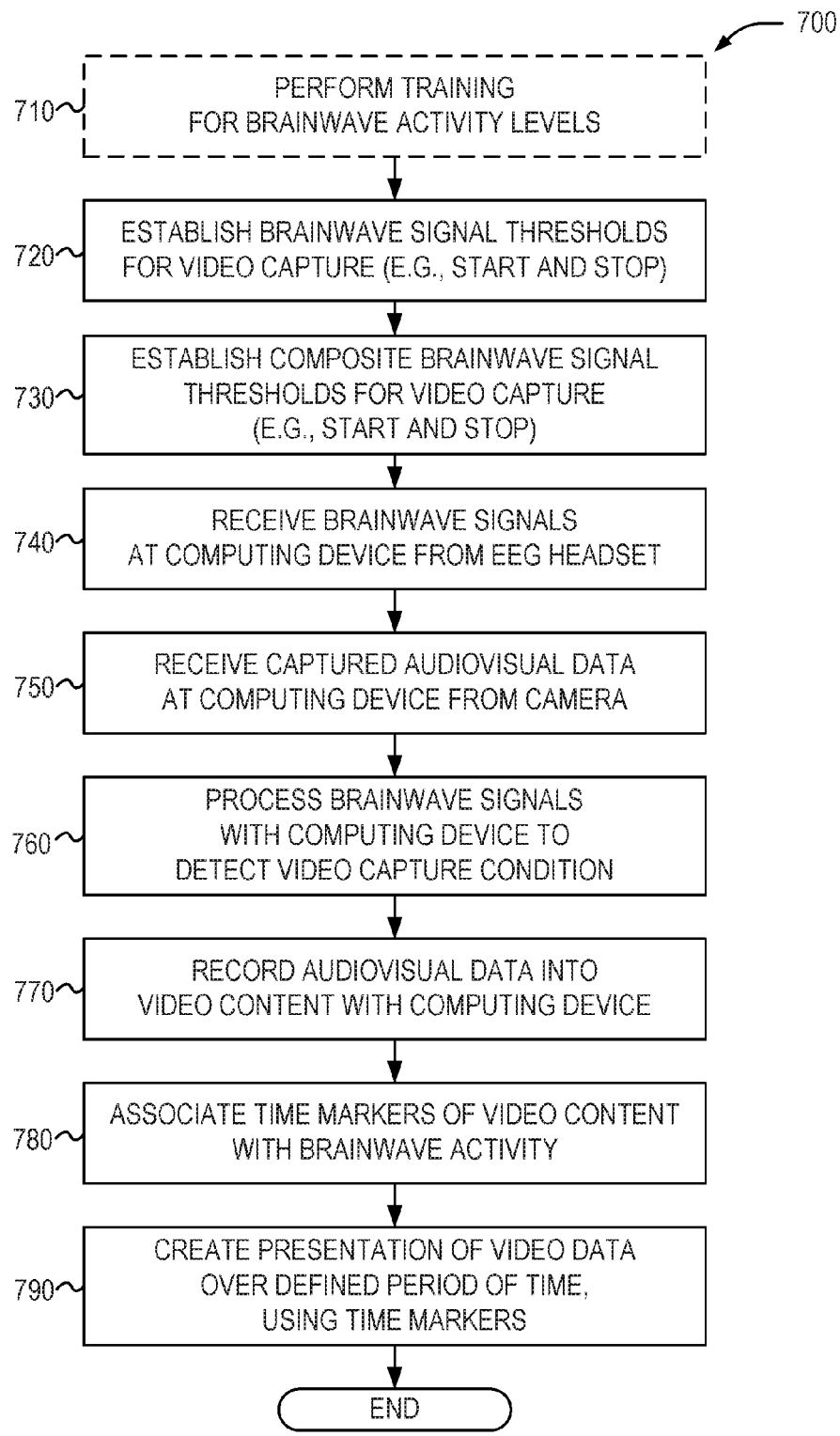
FIG. 7 illustrates a flowchart of a method for capture of video data with an EEG-based camera control technique, according to an example.

FIG. 7 illustrates a flowchart 700 of a method for capture of video data with an EEG-based camera control technique, according to an example. In an example, the method of flowchart 700 is executed by a computing device such as a mobile computing device (e.g., smartphone or tablet) that is connected to an externally located EEG headset and camera components. As shown, the flowchart 700 is indicated for the capture of a video image sequence (e.g., movie), but it will be understood that the following techniques may be modified for the production or extraction of still image frames or other derived static image data from such video or composite photo-audiovisual recordings. For example, in an example configuration, certain brainwave levels (e.g., alpha wave measurements) may be used for controlling video recording, while different brainwave levels (e.g., gamma) may be used for controlling image capture, in a simultaneous fashion.

As shown, the flowchart 700 optionally includes a performance of training for brainwave activity levels (operation 710), which may use the training techniques described above for still image captures (e.g., operation 610 of FIG. 6). In an example, the training includes learning and assignment procedures that are specific to training brain signals for identifying and invoking specific video recording controls.

The flowchart 700 further includes operations for establishing brainwave signal thresholds for a camera video capture operation (operation 720) for video recording commands such as start and stop video, and establishing composite brainwave signal thresholds for a camera video capture (operation 730) for these or other video recording commands. The brainwave signal thresholds may be obtained from the aforementioned training, provided as default values, or be partially or wholly user-controlled.

During operation of the EEG headset device, the mobile computing device may receive data for detected brainwave signals (operation 740) at the same time that the mobile computing device is receiving audiovisual data from a recording camera device (operation 750). The mobile computing device will proceed with processing operations for the detected brainwave signals (operation 760) to detect a video capture condition. As discussed herein, a detected video capture condition may be based on raw or composite brainwave levels that exceed a threshold at a point in time, over a period of time, or using other measurements.

In response to a detected video capture condition, the computing device may perform actions to proceed with recording the audiovisual content, or creating metadata to identify a period of interest within a stream of audiovisual content. These actions may include recording audiovisual data into a specific video content format on the computing device (operation 770) and associating time markers of the video content (and the recorded data) with specific markers of brainwave activity (operation 780). Based on the received audiovisual data and the stored metadata for the video content, the computing device may further store, process, or transmit the video content, such as creating a presentation (e.g., video clip) of audiovisual content collected over a defined period of time (operation 790).

In contrast to existing devices that only allow short images or sequences to be captured on a smartphone, the presently disclosed techniques are extendable for a variety of EEG devices, brainwave activity levels, and camera device embodiments. The presently disclosed techniques further allow for users to specify, select, and invoke a mental state of control for specific camera activities, beyond a simple interest level. Further, the presently disclosed techniques may be extended for the control of multiple external cameras at once, based on a coordination of communication signals and commands from a processing computing device. As a result, the camera device(s) that are controlled by an EEG headset need not be incorporated into the same circuitry as the EEG headset and computing device.

Figure 8:
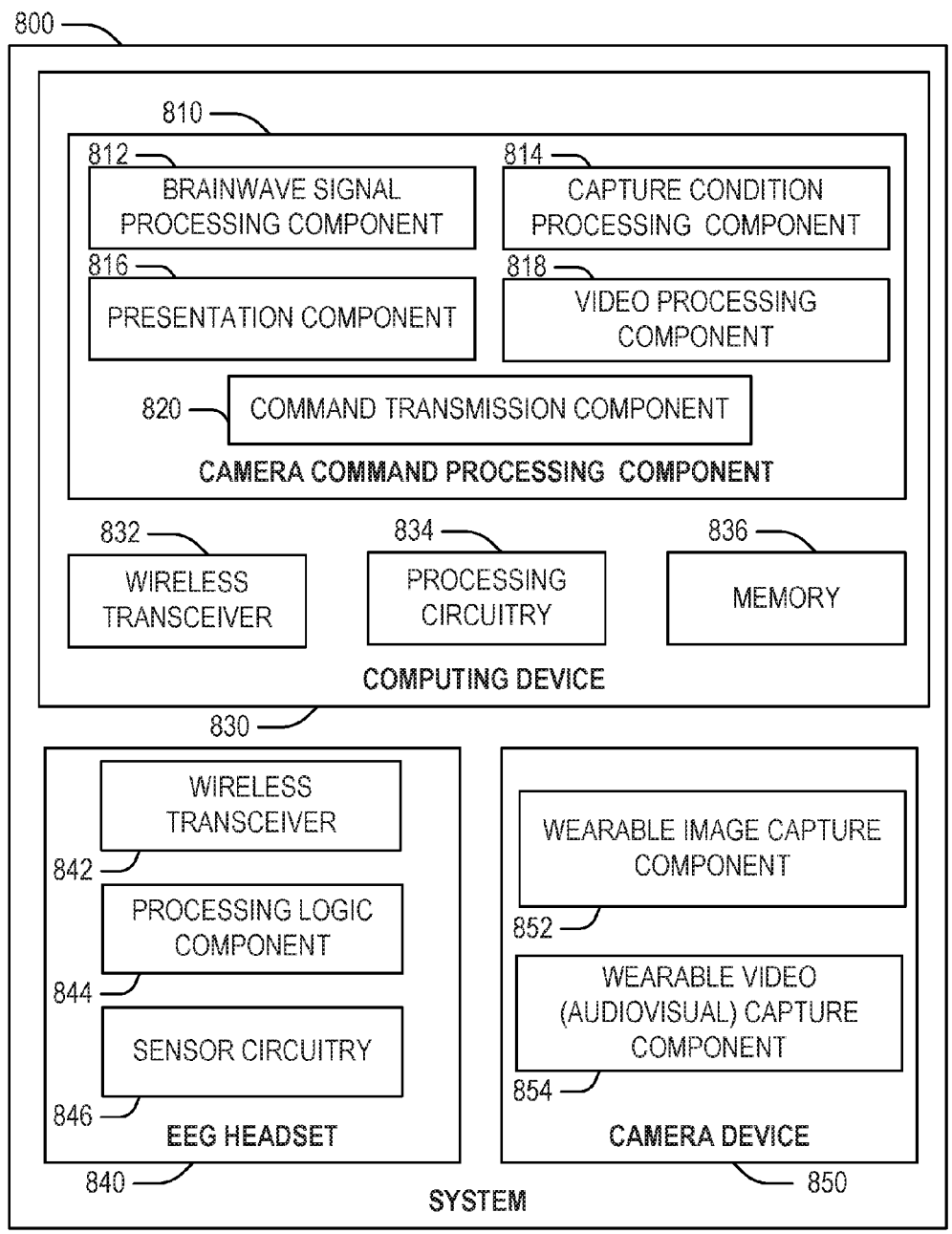
FIG. 8 illustrates a block diagram for an example system including a headset device, camera device, computing device, and camera command processing components, according to an example.

FIG. 8 is a block diagram illustrating an example system 800 including a headset device 840, a camera device 850, a computing device 830, a camera command processing component 810, and other circuitry and structural electronic components that may be configured for implementation of the techniques described herein. In accordance with the previous described configurations, the system 800 may embody the devices 830, 840, 850 in a single apparatus, or the respective devices may be separate apparatuses that are operably coupled (e.g., communicatively coupled) with one another.

The computing device 830 is depicted as including the camera command processing component 810, a wireless transceiver 832 (e.g., to perform wireless communications with the headset device 840 and the camera device 850), processing circuitry 834 (e.g., a central processing unit (CPU), system-on-chip, or microcontroller to operate software and logic for control of the camera command processing component 810), and memory 836 (e.g., volatile and storage memory). For example, the wireless transceiver 832 may wirelessly receive imaging data from the camera device 850 and brainwave data from the headset device 840 and such imaging data may be further processed with use of the processing circuitry 834 and the memory 836.

The camera command processing component 810 is depicted as including: a brainwave signal processing component 812, for example, to process the brainwave data received from the headset device 840; a capture condition processing component 814, for example, to determine a camera capture condition; a presentation component 816, for example, to create a presentation of multiple images collected over time from the imaging data; a video processing component 818, for example, to establish markers of a video clip from the imaging data based on brainwave activity; and a command transmission component 820, for examples, to transmit a command to the camera device 850 to perform a capture of imaging data, corresponding to a brainwave-based camera capture condition.

The headset device 840 is depicted as including: a wireless transceiver 842, for example, to wirelessly communicate brainwave signal data in raw or composite form to the computing device 810; a processing logic component 844, for example, to control sensor operations and detect composite brainwave conditions; and sensor circuitry 846, for example, to process raw electrical signals from the sensors and generate usable sensor output.

The camera device 850 is depicted as including: a wearable image capture component 852, for example, including an image sensor and static image capture functionality; and a wearable video capture component 854, for example, including an audio sensor and video processing circuitry for the capture of video and audio (e.g., movie) content. In other examples, the components of the camera device 850 may be provided in a non-wearable formats. The camera device 850 may further include a wired or wireless command component (not depicted) to receive commands from the computing device 830 or the headset device 840, to cause the capture of the audiovisual data, and to communicate the imaging data in return.

Figure 9:
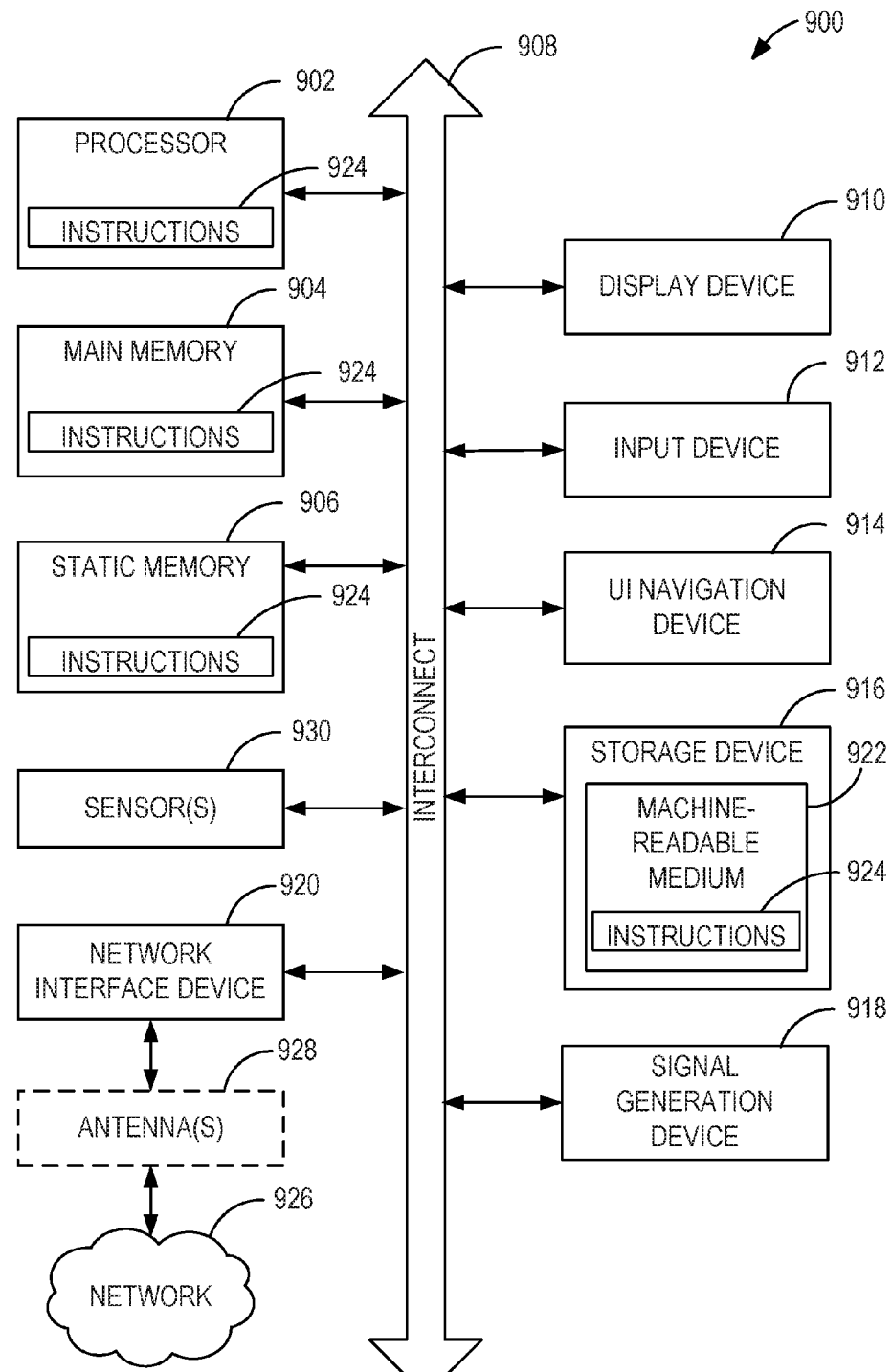
FIG. 9 illustrates a block diagram for an example computer system architecture upon which any one or more of the techniques (e.g., operations, processes, methods, and methodologies) discussed herein may be performed, according to an example.

FIG. 9 is a block diagram illustrating a machine in the example form of a computing system (e.g., computing device) 900, within which a set or sequence of instructions may be executed to cause the machine to perform any one of the methodologies discussed herein, according to an example embodiment. The machine may be a personal computer (PC), a tablet PC, a hybrid tablet/notebook PC, a personal digital assistant (PDA), a mobile telephone or smartphone, a wearable computer, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein. Similarly, the term "processor-based system" shall be taken to include any set of one or more machines that are controlled by or operated by a processor (e.g., a computer) to individually or jointly execute instructions to perform any one or more of the methodologies discussed herein.

Example computer system 900 includes at least one processor 902 (e.g., a central processing unit (CPU), a graphics processing unit (GPU) or both, processor cores, compute nodes, etc.), a main memory 904 and a static memory 906, which communicate with each other via an interconnect 908 (e.g., a link, a bus, etc.). The computer system 900 may further include a video display unit 910, an alphanumeric input device 912 (e.g., a keyboard), and a user interface (UI) navigation device 914 (e.g., a mouse). In one embodiment, the video display unit 910, input device 912 and UI navigation device 914 are incorporated into a touch screen display. The computer system 900 may additionally include a storage device 916 (e.g., a drive unit), a signal generation device 918 (e.g., a speaker), an output controller 932, a network interface device 920 (which may include or operably communicate with one or more antennas 928, transceivers, or other wireless communications hardware), and one or more sensors 930, such as a global positioning system (GPS) sensor, compass, accelerometer, location sensor, or other sensor.

The storage device 916 includes a machine-readable medium 922 on which is stored one or more sets of data structures and instructions 924 (e.g., software) embodying or utilized by any one or more of the methodologies or functions described herein. The instructions 924 may also reside, completely or at least partially, within the main memory 904, static memory 906, and/or within the processor 902 during execution thereof by the computer system 900, with the main memory 904, static memory 906, and the processor 902 also constituting machine-readable media.

While the machine-readable medium 922 is illustrated in an example embodiment to be a single medium, the term "machine-readable medium" may include a single medium or multiple media (e.g., a centralized or distributed database, and/or associated caches and servers) that store the one or more instructions 924. The term "machine-readable medium" shall also be taken to include any tangible medium that is capable of storing, encoding or carrying instructions for execution by the machine and that cause the machine to perform any one or more of the methodologies of the present disclosure or that is capable of storing, encoding or carrying data structures utilized by or associated with such instructions. The term "machine-readable medium" shall accordingly be taken to include, but not be limited to, solid-state memories, and optical and magnetic media. Specific examples of machine-readable media include non-volatile memory, including but not limited to, by way of example, semiconductor memory devices (e.g., electrically programmable read-only memory (EPROM), electrically erasable programmable read-only memory (EEPROM)) and flash memory devices; magnetic disks such as internal hard disks and removable disks; magneto-optical disks; and CD-ROM and DVD-ROM disks.

The instructions 924 may further be transmitted or received over a communications network 926 via an antenna 928 using a transmission medium via the network interface device 920 utilizing any one of a number of well-known transfer protocols (e.g., HTTP). Examples of communication networks include a local area network (LAN), a wide area network (WAN), the Internet, mobile telephone networks, plain old telephone (POTS) networks, and wireless data networks (e.g., Wi-Fi, 2G/3G, and 4G LTE/LTE-A or WiMAX networks). The term "transmission medium" shall be taken to include any intangible medium that is capable of storing, encoding, or carrying instructions for execution by the machine, and includes digital or analog communications signals or other intangible medium to facilitate communication of such software.

Embodiments used to facilitate and perform the techniques described herein may be implemented in one or a combination of hardware, firmware, and software. Embodiments may also be implemented as instructions stored on a machine-readable storage device, which may be read and executed by at least one processor to perform the operations described herein. A machine-readable storage device may include any non-transitory mechanism for storing information in a form readable by a machine (e.g., a computer). For example, a machine-readable storage device may include read-only memory (ROM), random-access memory (RAM), magnetic disk storage media, optical storage media, flash-memory devices, and other storage devices and media.

It should be understood that the functional units or capabilities described in this specification may have been referred to or labeled as components or modules, in order to more particularly emphasize their implementation independence. Such components may be embodied by any number of software or hardware forms. For example, a component or module may be implemented as a hardware circuit comprising custom very-large-scale integration (VLSI) circuits or gate arrays, off-the-shelf semiconductors such as logic chips, transistors, or other discrete components. A component or module may also be implemented in programmable hardware devices such as field programmable gate arrays, programmable array logic, programmable logic devices, or the like. Components or modules may also be implemented in software for execution by various types of processors. An identified component or module of executable code may, for instance, comprise one or more physical or logical blocks of computer instructions, which may, for instance, be organized as an object, procedure, or function. Nevertheless, the executables of an identified component or module need not be physically located together, but may comprise disparate instructions stored in different locations which, when joined logically together, comprise the component or module and achieve the stated purpose for the component or module.

Indeed, a component or module of executable code may be a single instruction, or many instructions, and may even be distributed over several different code segments, among different programs, and across several memory devices. Similarly, operational data may be identified and illustrated herein within components or modules, and may be embodied in any suitable form and organized within any suitable type of data structure. The operational data may be collected as a single data set, or may be distributed over different locations including over different storage devices, and may exist, at least partially, merely as electronic signals on a system or network. The components or modules may be passive or active, including agents operable to perform desired functions.

Additional examples of the presently described method, system, and device embodiments include the following, non-limiting configurations. Each of the following non-limiting examples may stand on its own, or may be combined in any permutation or combination with any one or more of the other examples provided below or throughout the present disclosure.

Example 1 is a method comprising electronic operations, which when performed by processor circuitry of a computing system, causes the computing system to perform the electronic operations including: receiving brainwave data from an electroencephalography (EEG) headset, the brainwave data representing a brainwave signal; processing the brainwave data to determine a camera capture condition; and transmitting a command to a camera device to perform a capture of imaging data with the camera device, the command corresponding to the camera capture condition.

In Example 2, the subject matter of Example 1 optionally includes, wherein the brainwave data represents a value for a raw brainwave measurement, the raw brainwave measurement representing a gamma, beta, alpha, theta, or delta brainwave.

In Example 3, the subject matter of any one or more of Examples 1-2 optionally include, wherein the brainwave data represents a composite value for a combination of raw brainwave measurements of multiple brainwaves, the multiple brainwaves including two or more of: gamma, beta, alpha, theta, or delta brainwaves.

In Example 4, the subject matter of Example 3 optionally includes, wherein the composite value corresponds to attention or meditation measurements.

In Example 5, the subject matter of any one or more of Examples 1-4 optionally include, wherein the camera capture condition relates to an image capture condition, wherein the camera device is operable to capture image data, and wherein the command causes the camera device to capture an image.

In Example 6, the subject matter of any one or more of Examples 1-5 optionally include, wherein the camera capture condition relates to a video capture condition, wherein the camera device is operable to record video data, and wherein the command causes the camera device to start capture or stop capture of a video.

In Example 7, the subject matter of any one or more of Examples 1-6 optionally include, wherein processing the brainwave data to determine the camera capture condition comprises: comparing the brainwave signal represented in the brainwave data to a brainwave signal threshold; and determining the camera capture condition in response to the brainwave signal exceeding the brainwave signal threshold.

In Example 8, the subject matter of Example 7 optionally includes, the electronic operations further including: performing training with a particular human user for brainwave activity levels of the particular human user, wherein the brainwave signal threshold is set as a result of the training.

In Example 9, the subject matter of any one or more of Examples 1-8 optionally include, the electronic operations further comprising: receiving the imaging data from the camera device, wherein the imaging data is received in response to the command to perform the capture of imaging data.

In Example 10, the subject matter of Example 9 optionally includes, wherein the imaging data includes data for multiple images, wherein the imaging data is received with a wireless communication from a wearable image capture device, the wireless communication occurring according to a BLUETOOTH® or IEEE 802.11 communication protocol.

In Example 11, the subject matter of Example 10 optionally includes, the electronic operations further comprising: creating a presentation of the multiple images collected over a defined period of time.

In Example 12, the subject matter of any one or more of Examples 9-11 optionally include, wherein the imaging data includes data for a video, wherein the imaging data is received with a wireless communication from a wearable video capture device, the wireless communication occurring according to a BLUETOOTH® or IEEE 802.11 communication protocol.

In Example 13, the subject matter of Example 12 optionally includes, the electronic operations further comprising: associating a first time marker of the video for a start of a video clip, based on brainwave activity; and associating a second time marker of the video for an end of the video clip, based on brainwave activity.

In Example 14, the subject matter of Example 13 optionally includes, the electronic operations further comprising: creating a presentation of the video collected over a defined period of time, the presentation of the video based on the first time marker and the second time marker.

In Example 15, the subject matter of any one or more of Examples 1-14 optionally include, the electronic operations further comprising: receiving second brainwave data from the EEG headset, the second brainwave data representing a second brainwave signal; processing the second brainwave data to determine a second camera capture condition; and transmitting a second command to the camera device to stop the capture of imaging data with the camera device, the command corresponding to the second camera capture condition; wherein the camera capture condition is to begin recording of a video; and wherein the second camera capture condition is to stop recording of the video.

In Example 16, the subject matter of Example 15 optionally includes, the electronic operations further comprising: receiving the imaging data from the camera device, the imaging data including data for the video, wherein the imaging data is received with a wireless communication from a wearable video capture device, the wireless communication occurring according to a BLUETOOTH® or IEEE 802.11 communication protocol.

Example 17 is at least one computer-readable storage medium comprising instructions to perform any of the methods of Examples 1-16.

Example 18 is an apparatus comprising means for performing any of the methods of Examples 1-16.

Example 19 is at least one non-transitory machine-readable medium comprising instructions for operation of a computer system, which when executed by the computer system, cause the computer system to perform electronic operations that: receive brainwave data from an electroencephalography (EEG) headset, the brainwave data representing a brainwave signal; process the brainwave data to determine a camera capture condition; and transmit a command to a camera device to perform a capture of imaging data with the camera device, the command corresponding to the camera capture condition.

In Example 20, the subject matter of Example 19 optionally includes instructions that cause the computer system to perform electronic operations that: process the brainwave data that represents a value for a raw brainwave measurement, the raw brainwave measurement representing a gamma, beta, alpha, theta, or delta brainwave.

In Example 21, the subject matter of any one or more of Examples 19-20 optionally include instructions that cause the computer system to perform electronic operations that: process the brainwave data that represents a composite value for a combination of raw brainwave measurements of multiple brainwaves, the multiple brainwaves including two or more of: gamma, beta, alpha, theta, or delta brainwaves.

In Example 22, the subject matter of any one or more of Examples 19-21 optionally include instructions that cause the computer system to perform electronic operations that: indicate an image capture condition with the camera capture condition, wherein the camera device is operable to capture image data, and wherein the command causes the camera device to capture an image.

In Example 23, the subject matter of any one or more of Examples 19-22 optionally include instructions that cause the computer system to perform electronic operations that: indicate a video capture condition with the camera capture condition, wherein the camera device is operable to record video data, and wherein the command causes the camera device to start capture or stop capture of a video.

In Example 24, the subject matter of any one or more of Examples 19-23 optionally include instructions that cause the computer system to perform electronic operations that: compare the brainwave signal represented in the brainwave data to a brainwave signal threshold; and determine the camera capture condition in response to the brainwave signal exceeding the brainwave signal threshold.

In Example 25, the subject matter of Example 24 optionally includes instructions that cause the computer system to perform electronic operations that: perform training with a particular human user for brainwave activity levels of the particular human user, wherein the brainwave signal threshold is set as a result of the training.

In Example 26, the subject matter of any one or more of Examples 19-25 optionally include instructions that cause the computer system to perform electronic operations that: receive the imaging data from the camera device, wherein the imaging data is received in response to the command to perform the capture of imaging data.

Example 27 is a system, comprising: a computing device, comprising: processing circuitry; a camera command processing component, operable with the processing circuitry, to: receive brainwave data from an electroencephalography (EEG) headset, the brainwave data representing a brainwave signal; process the brainwave data to determine a camera capture condition; and transmit a command to a camera device to perform a capture of imaging data with the camera device, the command corresponding to the camera capture condition.

In Example 28, the subject matter of Example 27 optionally includes: the camera device.

In Example 29, the subject matter of Example 28 optionally includes: the EEG headset.

In Example 30, the subject matter of any one or more of Examples 27-29 optionally include, the computing device further comprising: a wireless transceiver, operable with the processing circuitry, to: wirelessly receive the imaging data from the camera device, wherein the imaging data is received in response to the command to perform the capture of imaging data.

In Example 31, the subject matter of Example 30 optionally includes, a wearable image capture device, wherein the imaging data includes data for multiple images, wherein the imaging data is received with the wireless transceiver via a wireless communication from the wearable image capture device, the wireless communication occurring according to a BLUETOOTH® or IEEE 802.11 communication protocol.

In Example 32, the subject matter of Example 31 optionally includes, the camera command processing component to create a presentation of the multiple images collected over a defined period of time.

In Example 33, the subject matter of any one or more of Examples 30-32 optionally include, a wearable video capture device, wherein the imaging data includes data for a video, wherein the imaging data is received with the wireless transceiver via a wireless communication from the wearable video capture device, the wireless communication occurring according to a BLUETOOTH® or IEEE 802.11 communication protocol.

In Example 34, the subject matter of Example 33 optionally includes, the camera command processing component to associate a first time marker of the video for a start of a video clip, based on brainwave activity, and associate a second time marker of the video for an end of the video clip, based on brainwave activity.

In Example 35, the subject matter of Example 34 optionally includes, the camera command processing component to create a presentation of the video collected over a defined period of time, the presentation of the video based on the first time marker and the second time marker.

Example 36 is an apparatus, comprising: means for receiving brainwave data from an electroencephalography (EEG) headset, the brainwave data representing a brainwave signal; means for processing the brainwave data to determine a camera capture condition; and means for transmitting a command to a camera device to perform a capture of imaging data with the camera device, the command corresponding to the camera capture condition.

In Example 37, the subject matter of Example 36 optionally includes, means for processing the brainwave data that represents a value for a raw brainwave measurement, the raw brainwave measurement representing a gamma, beta, alpha, theta, or delta brainwave.

In Example 38, the subject matter of any one or more of Examples 36-37 optionally include, means for processing the brainwave data that represents a composite value for a combination of raw brainwave measurements of multiple brainwaves, the multiple brainwaves including two or more of: gamma, beta, alpha, theta, or delta brainwaves.

In Example 39, the subject matter of any one or more of Examples 36-38 optionally include, means for processing the camera capture condition that relates to an image capture condition, wherein the camera device is operable to capture image data, and wherein the command causes the camera device to capture an image.

In Example 40, the subject matter of any one or more of Examples 36-39 optionally include, means for processing the camera capture condition that relates to a video capture condition, wherein the camera device is operable to record video data, and wherein the command causes the camera device to start capture or stop capture of a video.

In Example 41, the subject matter of any one or more of Examples 36-40 optionally include, means for comparing the brainwave signal represented in the brainwave data to a brainwave signal threshold; and means for determining the camera capture condition in response to the brainwave signal exceeding the brainwave signal threshold.

In Example 42, the subject matter of Example 41 optionally includes, means for performing training with a particular human user for brainwave activity levels of the particular human user, wherein the brainwave signal threshold is set as a result of the training.

In Example 43, the subject matter of any one or more of Examples 36-42 optionally include, means for receiving the imaging data from the camera device, wherein the imaging data is received in response to the command to perform the capture of imaging data.

In Example 44, the subject matter of any one or more of Examples 36-43 optionally include, means for receiving second brainwave data from the EEG headset, the second brainwave data representing a second brainwave signal; means for processing the second brainwave data to determine a second camera capture condition; and means for transmitting a second command to the camera device to stop the capture of imaging data with the camera device, the command corresponding to the second camera capture condition; wherein the camera capture condition is to begin recording of a video; and wherein the second camera capture condition is to stop recording of the video.

In Example 45, the subject matter of Example 44 optionally includes: means for receiving the imaging data from the camera device, the imaging data including data for the video, wherein the imaging data is received with a wireless communication from a wearable video capture device, the wireless communication occurring according to a BLUETOOTH® or IEEE 802.11 communication protocol.

In the above Detailed Description, various features may be grouped together to streamline the disclosure. However, the claims may not set forth every feature disclosed herein as embodiments may feature a subset of said features. Further, embodiments may include fewer features than those disclosed in a particular example. Thus, the following claims are hereby incorporated into the Detailed Description, with a claim standing on its own as a separate embodiment.

What is claimed is:

1. A computing device, comprising:
   processing circuitry; and
   a camera command processing component, operable with the processing circuitry, to:
   receive brainwave data from an electroencephalography (EEG) headset, the brainwave data including a composite brainwave value that represents a combination of raw brainwave measurements of multiple brainwaves including two or more of: gamma, beta, alpha, theta, or delta brainwaves;
   process the composite brainwave value to identify a user mental state, wherein the user mental state is identified by the composite brainwave value exceeding a threshold value;
   determine a camera capture condition based on the identified user mental state; and
   transmit a command to a camera device to perform a capture of imaging data with the camera device, the command corresponding to the camera capture condition.

2. The computing device of claim 1, the computing device further comprising:
   a wireless transceiver, operable with the processing circuitry, to:
   wirelessly receive the imaging data from the camera device, wherein the imaging data is received in response to the command to perform the capture of imaging data.

3. The computing device of claim 2, further comprising:
   a wearable image capture device, wherein the imaging data includes data for multiple images, wherein the imaging data is received with the wireless transceiver via a wireless communication from the wearable image capture device, the wireless communication occurring according to a wireless personal area network or wireless local area network communication protocol.

4. The computing device of claim 3, the camera command processing component to create a presentation of the multiple images collected over a defined period of time.

5. The computing device of claim 2, further comprising:
   a wearable video capture device, wherein the imaging data includes data for a video, wherein the imaging data is received with the wireless transceiver via a wireless communication from the wearable video capture device, the wireless communication occurring according to a wireless personal area network or wireless local area network communication protocol.

6. The computing device of claim 5, the camera command processing component to associate a first time marker of the video for a start of a video clip, based on brainwave activity, and associate a second time marker of the video for an end of the video clip, based on brainwave activity.

7. The computing device of claim 6, the camera command processing component to create a presentation of the video collected over a defined period of time, the presentation of the video based on the first time marker and the second time marker.

8. At least one non-transitory machine-readable medium comprising instructions for operation of a computer system, which when executed by the computer system, cause the computer system to perform electronic operations that:
receive brainwave data from an electroencephalography (EEG) headset, the brainwave data including a composite brainwave value that represents a combination of raw brainwave measurements of multiple brainwaves, the multiple brainwaves including two or more of: gamma, beta, alpha, theta, or delta brainwaves;
process the composite brainwave value to identify a user mental state, wherein the user mental state is identified by the composite brainwave value exceeding a threshold value;
determine a camera capture condition based on the identified user mental state; and
transmit a command to a camera device to perform a capture of imaging data with the camera device, the command corresponding to the camera capture condition.

9. The machine-readable medium of claim 8 wherein the brainwave data further includes a value for a raw brainwave measurement, the raw brainwave measurement representing a gamma, beta, alpha, theta, or delta brainwave, and wherein the user mental state is further identified by the raw brainwave measurement.

10. The machine-readable medium of claim 8, comprising instructions that cause the computer system to perform electronic operations that:
indicate an image capture condition with the camera capture condition, wherein the camera device is operable to capture image data, and wherein the command causes the camera device to capture an image.

11. The machine-readable medium of claim 8, comprising instructions that cause the computer system to perform electronic operations that:
indicate a video capture condition with the camera capture condition, wherein the camera device is operable to record video data, and wherein the command causes the camera device to start capture or stop capture of a video.

12. The machine-readable medium of claim 8, comprising instructions that cause the computer system to perform electronic operations that:
perform training with a particular human user for brainwave activity levels of the particular human user, wherein the threshold value is set as a result of the training.

13. The machine-readable medium of claim 8, comprising instructions that cause the computer system to perform electronic operations that:
receive the imaging data from the camera device, wherein the imaging data is received in response to the command to perform the capture of imaging data.

14. A method comprising electronic operations, which when performed by processor circuitry of a computing system, causes the computing system to perform the electronic operations including:
receiving brainwave data from an electroencephalography (EEG) headset, the brainwave data including a composite brainwave value that represents a combination of raw brainwave measurements of multiple brainwaves, the multiple brainwaves including two or more of: gamma, beta, alpha, theta, or delta brainwaves;
processing the composite brainwave value to identify a user mental state, wherein the user mental state is identified by the composite brainwave value exceeding a threshold value;
determining a camera capture condition based on the identified user mental state; and
transmitting a command to a camera device to perform a capture of imaging data with the camera device, the command corresponding to the camera capture condition.

15. The method of claim 14, wherein the brainwave data also includes a value for a raw brainwave measurement, the raw brainwave measurement representing a gamma, beta, alpha, theta, or delta brainwave.

16. The method of claim 14, wherein the camera capture condition relates to an image capture condition, wherein the camera device is operable to capture image data, and wherein the command causes the camera device to capture an image.

17. The method of claim 14, wherein the camera capture condition relates to a video capture condition, wherein the camera device is operable to record video data, and wherein the command causes the camera device to start capture or stop capture of a video.

18. The method of claim 14, the electronic operations further including:
performing training with a particular human user for brainwave activity levels of the particular human user, wherein the threshold value is set as a result of the training.

19. The method of claim 14, the electronic operations further comprising:
receiving the imaging data from the camera device, wherein the imaging data is received in response to the command to perform the capture of imaging data.

20. The method of claim 14, the electronic operations further comprising:
receiving second brainwave data from the EEG headset, the second brainwave data including a second composite brainwave value that represents a combination of raw brainwave measurements of multiple brainwaves, the multiple brainwaves including two or more of: gamma, beta, alpha, theta, or delta brainwaves;
processing the second composite brainwave value a identify a second user mental state, wherein the second user mental state is identified by the second composite brainwave value exceeding a second threshold value;
determining a second camera capture condition based on the identified second user mental state; and
transmitting a second command to the camera device to stop the capture of imaging data with the camera device, the command corresponding to the second camera capture condition;
wherein the camera capture condition is to begin recording of a video; and
wherein the second camera capture condition is to stop recording of the video.

21. The method of claim 20, the electronic operations further comprising:
receiving the imaging data from the camera device, the imaging data including data for the video, wherein the imaging data is received with a wireless communication from a wearable video capture device, the wireless communication occurring according to a wireless personal area network or wireless local area network communication protocol.

22. The computing device of claim 1, the camera command processing component to process the composite brainwave value to determine respective commands to transmit to the camera device, wherein the respective commands, triggered based on associated composite brainwave values, include capturing an image or begin recording of a video.

23. The computing device of claim 5, the camera command processing component to generate a composite video comprising of a series of video clips taken from the video based on the brainwave data, wherein the video clips are selected based on the brainwave data at a time of a video capture condition.

24. The computing device of claim 1, wherein the command causes the camera device to capture an image, and wherein transmission of the command is determined based on brainwave data associated with a user defined interest indicator.

25. The machine-readable medium of claim 8, comprising instructions that cause the computer system to perform electronic operations that:
process the composite brainwave value to determine respective commands to transmit to the camera device, wherein the respective commands, triggered based on associated composite brainwave values, include capturing an image or begin recording of a video.

26. The machine-readable medium of claim 11, comprising instructions that cause the computer system to perform electronic operations that:
generate a composite video comprising of a series of video clips taken from the video based on the brainwave data, wherein the video clips are selected based on the brainwave data at a time of the video capture condition.

27. The machine-readable medium of claim 8, wherein the command causes the camera device to capture an image, and wherein transmission of the command is determined based on brainwave data associated with a user defined interest indicator.

28. The method of claim 14, the electronic operations further comprising:
processing the composite brainwave value to determine respective commands to transmit to the camera device, wherein the respective commands, triggered based on associated composite brainwave values, include capturing an image or begin recording of a video.

29. The method of claim 17, the electronic operations further comprising:
generating a composite video comprising of a series of video clips taken from the video based on the brainwave data, wherein the video clips are selected based on the brainwave data at a time of the video capture condition.

30. Time method of claim 14, wherein the command is transmitted to the camera device to capture an image, wherein transmission of the command is determined based on brainwave data associated with a user defined interest indicator.

* * * * *

UNITED STATES PATENT AND TRADEMARK OFFICE
CERTIFICATE OF CORRECTION

PATENT NO. : 9,712,736 B2  
APPLICATION NO. : 14/970066  
DATED : July 18, 2017  
INVENTOR(S) : Kearns et al.

Page 1 of 1

It is certified that error appears in the above-identified patent and that said Letters Patent is hereby corrected as shown below:

On the Title Page

In item (73), in "Assignee", in Column 1, Line 1, delete "Coprporation," and insert --Corporation,-- therefor In the Claims In Column 20, Line 54, in Claim 20, delete "a" and insert --to-- therefor In Column 22, Line 28, in Claim 30, delete "Time" and insert --The-- therefor Signed and Sealed this
Twenty-fifth Day of June, 2019

Andrei Iancu
*Director of the United States Patent and Trademark Office*